US010076767B2

(12) United States Patent
Offermann

(10) Patent No.: US 10,076,767 B2
(45) Date of Patent: Sep. 18, 2018

(54) METERING DEVICE FOR METERING A LIGHT-CURING MATERIAL IN A MANUALLY CONTROLLED MANNER

(71) Applicant: Anke Viering, Munich (DE)

(72) Inventor: Thomas Offermann, Eppan (IT)

( * ) Notice: Subject to any disclaimer, the term of this patent is extended or adjusted under 35 U.S.C. 154(b) by 67 days.

(21) Appl. No.: 14/905,732

(22) PCT Filed: Jul. 16, 2014

(86) PCT No.: PCT/EP2014/065291
§ 371 (c)(1),
(2) Date: Jan. 15, 2016

(87) PCT Pub. No.: WO2015/007792
PCT Pub. Date: Jan. 22, 2015

(65) Prior Publication Data
US 2016/0158791 A1    Jun. 9, 2016

(30) Foreign Application Priority Data

Jul. 16, 2013   (DE) .......................... 10 2013 107 548

(51) Int. Cl.
*B05C 17/00*       (2006.01)
*A61C 5/62*        (2017.01)
(Continued)

(52) U.S. Cl.
CPC .............. *B05C 17/00* (2013.01); *G03F 7/16* (2013.01); *G03F 7/2051* (2013.01); *A61C 5/62* (2017.02)

(58) Field of Classification Search
CPC ........ A61C 5/62; A61C 19/004; B43K 29/10; B05C 9/08
See application file for complete search history.

(56) References Cited

U.S. PATENT DOCUMENTS 9,883,931 B2 *   2/2018   Gente ...................... A61C 5/55
2008/0118887 A1 *  5/2008  Teufelberger ........ A61C 19/004
                                                      433/29
(Continued)

FOREIGN PATENT DOCUMENTS

DE     20 2011 109 785 U1    6/2012
DE     10 2011 054 959 A1    5/2013
(Continued)

OTHER PUBLICATIONS

PCT/EP2014/065291, International Search Report, dated Feb. 12, 2014.
DE 10 2013 107 548.7, Search Report, dated Feb. 25, 2014.

*Primary Examiner* — Jennifer C Chiang
*Assistant Examiner* — Bradley Oliver
(74) *Attorney, Agent, or Firm* — Abel Law Group, LLP

(57) ABSTRACT

An apparatus for metering a light-curing material, comprising a housing section; wherein the housing section comprises at least a first end section and a second end section arranged opposite to said first section a receiving device for receiving, in a detachable manner, a metering device, in which the light-curing material is contained; wherein the metering device comprises an outlet opening out of which the light-curing material may exit, a light-emitting device for curing the light-curing material, in particular an LED lamp and/or a flashlight device; wherein the receiving device is designed such that the outlet opening of the metering device faces the first end section after being connected to the receiving device; wherein the light-emitting device is arranged in or on the first end section of the housing section in order to be able to provide light towards or in the direction of the first end section of the housing.

14 Claims, 3 Drawing Sheets

(51) Int. Cl.
*G03F 7/16* (2006.01)
*G03F 7/20* (2006.01)

(56) References Cited

U.S. PATENT DOCUMENTS

| | | | | |
|---|---|---|---|---|
| 2010/0233646 | A1* | 9/2010 | Brokx | A61C 5/62 |
| | | | | 433/36 |
| 2017/0231734 | A1* | 8/2017 | Jurcevic | A61C 19/004 |
| | | | | 433/29 |
| 2018/0071052 | A1* | 3/2018 | Li | A61C 5/55 |
| 2018/0110587 | A1* | 4/2018 | Pruett | A61C 5/00 |

FOREIGN PATENT DOCUMENTS

| | | |
|---|---|---|
| DE | 20 2012 100 929 U1 | 8/2013 |
| DE | 10 2013 102 654 A1 | 9/2013 |
| DE | 20 2013 100 497 U1 | 12/2013 |
| WO | 2013/064248 A2 | 5/2013 |

* cited by examiner

METERING DEVICE FOR METERING A LIGHT-CURING MATERIAL IN A MANUALLY CONTROLLED MANNER

The present invention relates to a metering apparatus for the manually-controlled metering of a light-curing material according to claim 1.

Materials of different viscosities are metered by means of a metering apparatus for various purposes. The materials may be fluid, semi-fluid, in a form of a paste and so on. The metering apparatus, depending on application and purpose of use, may be operated in fully-automated, partly-automated or manual manner. An example of a manually-operated metering apparatus is disclosed in DE 10 2011 054 959 A1.

It is an object of the present invention to propose a further metering apparatus.

Said object according to the present invention is achieved by a metering apparatus having the features of claim 1.

Thus, a metering apparatus for the manually-controlled metering of a light-curing material comprising at least one housing section (optionally referred to as housing) is proposed by the present invention. The housing section comprises at least one first end section (or one first end) and one second end section (or one second end) arranged opposite to it.

The housing section further comprises a receiving device for detachably receiving at least one metering device, wherein the light-curing material is provided in the metering device, and wherein the metering device comprises an outlet opening out of which the light-curing material may exit.

The housing section further comprises a light-emitting device for curing the light-curing material after it has been dispensed from the metering device through the outlet opening.

The receiving device is thereby designed such that the outlet opening of the metering device—after being connected as intended to the receiving device—faces the first end section, or such that the light-curing material, when applied or used as intended, may be applied in an outlet area which lies in the area of the first end section, in any case however not in the area of the second end section.

In this, the light-emitting device is arranged in or on the first end section of the housing section. Additionally or alternatively, it is arranged to provide, when being actuated, light—preferably only—towards the first end section of the housing.

In all of the embodiments, the use of the expression "may be" or "may have" and so on, is to be understood synonymously with "preferably is" or "preferably has," and so on respectively, and is intended to illustrate an embodiment according to the present invention.

Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" always as "at least one". This understanding is also equally encompassed by the present invention as the interpretation that a numeric word, for example, "one" may alternatively mean "exactly one", wherever this is evidently technically possible for the person skilled in the art. Both are encompassed by the present invention and apply herein to all used numerical words.

Developments of the present invention are each subject-matter of dependent claims and embodiments.

Embodiments according to the present invention may comprise one or more of the following features in any arbitrary combination.

In certain embodiments according to the present invention, the metering apparatus is designed to receive the light-emitting device detachably. In others, the light-emitting device is not detachably received.

The housing section comprises in some embodiments according to the present invention an actuation device for switching on and/or switching off the light-emitting device. The actuation device may be actuated manually, e.g. by using the middle finger; it may enable an on/off function and/or the continuous operation.

In certain embodiments according to the present invention, the receiving device comprises, for detachably receiving at least one metering device, only or exclusively one first holding section—in any case however no second holding section—by means of which the metering device is clamped at the housing section or is connected to the housing section by means of threading, latching, bayonet fixing or the like.

In some embodiments according to the present invention, the receiving device comprises, for detachably receiving at least one metering device—at least or exclusively—one first holding section and one second holding section. In this, the first holding section is arranged closer to the first end section than is the second holding section. At the same time at least the first and/or the second holding section comprise(s) an adaption section movable in a longitudinal direction of the housing section.

In certain embodiments according to the present invention, the adaption section, movable in a longitudinal direction of the housing section, comprises or consists of at least one spring element, one spring or one elastical element, e.g. a leaf or spiral spring.

In some embodiments according to the present invention, at least the first and/or the second holding section comprises a ring-shaped or cylinder-shaped section for embracing or enfolding the metering device along a part of the circumference thereof. The ring-shaped or cylinder-shaped section has a slot or it leaves or allows a free slot between two of its sections. In the area of said slot, the holding section does not embrace or enfold the circumference of the metering device.

In certain embodiments according to the present invention, the housing section comprises a housing back and a housing bottom side. The first and the second holding section are, in some embodiments according to the present invention, parts of the housing bottom side or correspond thereto or are arranged on it.

In some embodiments according to the present invention, the first and the second holding sections are arranged such that they embrace or enfold a front and a back end section (or a front and a back end) of the metering device, however not a section being between the front and the back end section, for example a middle section thereof.

In certain embodiments according to the present invention, the housing section comprises a housing back and a housing bottom side. The actuation device for switching on/off the light-emitting device is in some embodiments according to the present invention part of the housing back or corresponds thereto or is arranged on it.

In some embodiments according to the present invention, the actuation device for switching on/off the light-emitting device is not arranged at a distance being farther to the first end section than to the first and/or the second holding section, with respect to the longitudinal direction of the housing section or of the metering apparatus.

In certain embodiments according to the present invention, the light-emitting device comprises an optical lens or it is arranged to emit light through such lens.

In some embodiments according to the present invention, the voltage source for the light-emitting device in arranged in the second end section.

In certain embodiments according to the present invention, the voltage source is a battery.

In some embodiments according to the present invention, the voltage source is designed to be charged by induction.

In some embodiments according to the present invention, the receiving device is arranged such that a light-curing material exiting out of the outlet opening of a metering device received in said receiving device is applied into a light cone of the light-emitting device (when being in use).

In some embodiments according to the present invention, the housing section comprises, at its first end section, a protrusion whose diameter or any cross section thereof is less than a diameter of the housing section in the area of its first and/or its second holding section, or a cross section thereof.

In some embodiments according to the present invention, the end section is beak-shaped or is stretched.

In some embodiments according to the present invention, the end section protrudes in a longitudinal direction beyond the first holding section.

In some embodiments according to the present invention, the metering apparatus comprises at least one metering device received in the housing section.

In certain embodiments according to the present invention, the metering device comprises a metering channel.

In some embodiments according to the present invention, the metering device and/or the metering channel comprises a detachable lock.

In specific embodiments according to the present invention, the metering channel is made of or comprises metal.

In some embodiments according to the present invention, preferably only or exclusively an outlet opening of the metering channel and an outlet surface (e.g. a glass surface, a lens surface or the like), through which the light emitted out of the light-emitting device passes, is provided in the first end section.

In certain embodiments according to the present invention, a straight line, which connects the outlet opening of the metering channel to an outlet surface (e.g. a glass surface, a lens surface or the like), passes through an area in which there is no section of the housing section.

In certain embodiments according to the present invention, the metering device comprises a metering channel through which the light-curing material is extracted or applied. Thereby, the metering device—in particular preferably completely or substantially—is made of or comprises a first material, whereas the metering channel—in particular preferably completely or substantially—is made of or comprises a second material. The second material differs from the first material.

The reservoir is in certain embodiments according to the present invention designed as a container or as an interior of a cartridge.

In certain embodiments according to the present invention, the metering device is connected to the metering channel in a detachable manner.

In specific embodiments according to the present invention, the metering channel is plugged onto the metering device or onto its cover by means of a Luer-lock system.

In some embodiments according to the present invention, the metering device comprises a sealing device, e.g. a sealing ring being exemplarily an O-ring. By means of the sealing device, it is advantageously possible to achieve a seal between the metering device or the reservoir on the one hand and a cover of the metering device on the other hand, against an exterior or the environment or an outside.

In certain embodiments according to the present invention, the cover of the metering device, out of which the metering channel extends or which comprises the latter, is made of, with respect to the metering device, a harder material, or at least comprises a harder material. This design may advantageously contribute or guarantee in some embodiments that the seal is sustained between the metering device and its exterior in the area of the cover also upon elastic deformation of the metering device, for example, upon applying pressure thereon.

In some embodiments according to the present invention, the housing section is made of the same material (e.g., polyethylene (PE)) as the reservoir itself, or it comprises such material.

In certain embodiments according to the present invention, the light-emitting device is connected to or comprises at least one optical fiber (glass fiber, etc.), which guides or conducts the light from the light-emitting device (which may be arranged in a second end section of the housing section) to the first end section or near an outlet opening of the metering device.

In some embodiments according to the present invention, the housing section is made of a metal (aluminum, stainless steel, titanium, etc.) or comprises such material.

In certain embodiments according to the present invention, an internal gas cartridge and/or another device is provided to build up pressure in order to increase the pressure within the reservoir. This may be advantageous for a more comprehensive emptying of the reservoir. Furthermore, this may allow also an overhead working with the metering apparatus according to the invention.

In some embodiments according to the present invention, the reservoir comprises in at least a section thereof and/or in its lateral surface or in a main area thereof, respectively, a wall thickness in a range of 0.75 to 1.25 mm, preferably from 0.9 to 1.1 mm, again preferably in a range from 0.95 to 1.05 mm. These ranges have been found to be particularly suitable with regard to the desired ductility and the required stability and capacity.

In certain embodiments according to the present invention, the metering device comprises light-curing material which cures by means of radiation in a range of 380 to 500 nanometers (nm), in particular in the range of 450 to 480 nm, particularly at 470 nm, and in particular in a range of 390 to 410 nm, particularly at 405 nm.

In some embodiments according to the present invention, the reservoir is made of a light impermeable material. The light impermeable material is preferably, at least, or particularly impermeable to a radiation range of 380 to 500 nanometers (nm), in particular in the range of 450 to 480 nm, particularly at 470 nm, and in particular in a range of 390 to 410 nm, particularly at 405 nm.

In certain embodiments according to the present invention, the metering device and/or the metering channel comprise a detachable closure against an exterior (i.e. the environment). In some embodiments according to the invention, the closure is a cap.

In some embodiments according to the present invention, the closure is impermeable to light, preferably for a radiation range of 380 to 500 nanometers (nm), in particular in the range of 450 to 480 nm, particularly at 470 nm, and in particular in a range of 390 to 410 nm, particularly at 405 nm.

In some embodiments according to the present invention, the light emitting device for curing the light-curing material is an LED lamp and/or a flash light means or comprises the like.

In certain embodiments according to the present invention, the housing section is embodied to receive the light emitting device in a detachable manner. This can be done for example by inserting, clicking, seizing, clamping or the like. The housing may be prepared or provided accordingly.

In specific embodiments according to the present invention, the housing section and the metering device, in particular the cover of the metering apparatus comprise a bayonet closure or corresponding parts of a bayonet closure for receiving the metering device in or on the housing section in a detachable manner.

In some embodiments according to the present invention, the metering device or the housing section, comprises a device for receiving the light-emitting device in a detachable manner. This device is embodied in some embodiments according to the present invention as a snap-on device. In other embodiments according to the invention, this device is embodied as a plug device and the like.

In some embodiments according to the present invention, the light-emitting device comprises an actuation device (a switch or the like), by means of which it can be brought in a continuous emitting operation state.

In certain embodiments according to the present invention, the light-emitting device comprises an actuation device or is connected thereto in fluid communication, by means of which it can be brought in an emitting operation state, by a pressure applied thereon, which lasts only for the time period in which the pressure is applied or exists. This can be effected by means of a pressure switch with a reset device.

Any embodiments according to the present invention may comprise or offer one or more of the following advantages.

Thus, there is an advantage in the interchangeability of metering devices, being utilized or emptied through use, whose reservoir does not comprise enough light-curing material anymore. The housing section and all other components may be preserved and may further be used. Only the metering device with the reservoir is to be replaced. This advantageously reduces the material costs, disposal costs, the need for storage space and the like. Here, even the cover may further be used due to the separability or detachability of reservoir and cover in some embodiments according to the present invention.

The metering channel and the light-emitting device—different than for example the metering apparatuses known from DE 10 2011 054 959 A1—are not arranged or provided in the present invention at two end sections of the metering device or of the housing section lying opposite, but at the same end section. Thus, after having applied the light-curing material on e.g. a repair site, it is not required to rotate the metering device to irradiate said repair site in order to cure the applied material by means of the light-emitting device. A rotation of the metering device during use may be omitted according the present invention. With that, omitted is also the redistribution, which may be also referred to as backflow, of the light-curing material in the reservoir due to the regular rotation observed by the metering apparatus of the prior art, and which—in particular by non-completely filled reservoir—leads to the known phenomena of the half-empty ketchup bottle. Such phenomena is manifested in that the user must wait a while, after having used the light-emitting device, arranged at the opposite end, until the light-curing material has again gathered in sufficient quantity the end of the reservoir comprising the metering channel. This may complicate the handling of the metering apparatus of the prior art in particular by viscous light-curing material. In addition, the ultimately applied light-curing material may be mixed with air bubbles due to the frequent rotation of the metering apparatus when being used. This impairs the clean and the constant application of the light-curing material. These disadvantages do not occur or occur considerably less by the present invention.

At the same time, the one-hand operation of the metering apparatus according to the present invention is advantageously possible up to, and including, the curing. It is not required by the present invention to lighten the light-curing material applied by a metering apparatus using one hand by a light-emitting device using the other hand. The second hand may instead be used for holding the work piece, by way of example.

The bayonet closure proposed herein for some embodiments according to the present invention has proved its particular suitability to grant a quick, easy and reliable interchangeability.

In a number of embodiments according to the present invention, different components are made of different materials or comprise such material. Hereby a further advantageous contribution to the tightness of the metering apparatus against an exterior may be achieved.

A tightness between the individual components is advantageously achieved according to the present invention with the sealing device proposed herein.

The provision of different materials may also advantageously allow the different components of the metering apparatus, independent from each other and in terms of their respective function, to be produced in the most cost-effective manner, respectively.

The present invention is hereinafter exemplarily explained with respect to the accompanying drawings, in which identical reference numerals denote the same or similar components. In the figures.

Figure 1:
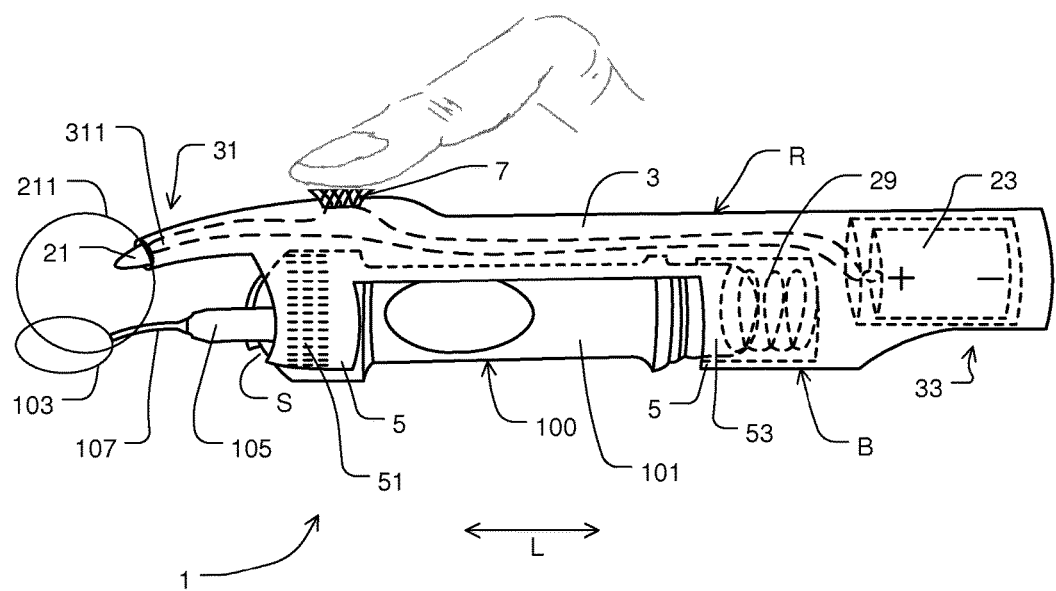
FIG. 1 shows a side view of a metering apparatus according to the present invention in a first embodiment.

FIG. 1 shows a side view of a metering apparatus 1. The latter comprises a housing section 3 and a metering device 100. The longitudinal direction or length of the metering apparatus 1 and of the housing section 3 is marked with double arrow L.

The housing section 3 comprises a housing rear R and a housing bottom side B. The housing section 3 further comprises a first end section 31 (see the left end of the housing section 3, with respect to the illustration of FIG. 1) and a second end section 33 (right end in FIG. 1).

A receiving device 5 is embodied in the area of the housing bottom side B. It serves the detachable reception of the metering device 100.

In the example of FIG. 1, the receiving device 5 consists of a first holding section 51 and a second holding section 53. The first holding section 51 is closer to the first end section 31 than the second holding section 53. The first holding section 51 is arranged at a distance farther to the second end section 33 than is the second holding section 53.

The first holding section 51 together with the second holding section 53 hold the metering device 100 at the housing section 3.

The receiving device 5 may comprise more components than shown here. It may also further comprise only one holding section, optionally the first or the second. Such embodiment, likewise according to the present invention, is however not shown in any of the figures.

In the purely exemplary illustration of FIG. 1, the receiving device 5 is embodied in order to allow to first press the metering device 100, against the effect of the spring element 29, from left (with respect to the illustration of FIG. 1) to right into the second holding section 53. Subsequently, a front area or an outlet area of the metering device 100 may be moved through a slot S in the first holding section 51 towards to top, i.e. in the direction of the housing rear R. If the spring element 29 is subsequently, at least partially, released or loosened by carefully releasing the metering device 100, then the spring element 29 presses or pushes the metering device 100 against the interior of the at least partially ring-shaped holding section 31 which narrows or tapers to the left. The metering device 100 is thus clamped by means of the first and the second holding section 31, 33, and between them. If the metering device 100 is pressed against the effect of the spring element 29 to the right or towards the second holding section 53, then the metering device may be also released or removed from the metering apparatus 1.

The spring element 29 has its share in that metering devices 100 having different lengths may be received into the housing section 3. For example, when a metering device is used, instead of the metering device 100 shown in FIG. 1, that is about 10% longer, then the spring element 29 is under higher tension than the example shown in FIG. 1, upon inserting the metering device into the housing section 3 and afterwards. A part of the spring element 29 may move and, thus, adapt the holding device 5 to the length of the metering device 100. Therefore, the spring element 29 may also be referred to as adaption section.

The provision of an adaption section, which is not a spring element, is equally encompassed by the present invention. Hence, the adaption section may be e.g. a mechanically adjustable device like a knurled screw, spindle or the like.

The receiving device 5 may further be designed to receive, one after the other, metering devices 100 which differ from each other not only in their length, but (also) in their thickness or in their cross section. This is exemplarily already possible with the first and second holding sections 51, 53 shown in FIG. 1. Due to that, the metering apparatus 1 is advantageously suitable to receive or to be used with metering devices 100 that have different volumes of light-curing material.

The receiving device 5 is embodied to embrace or enfold a back end section of the metering device 100, not however an end (middle) section thereof disposed between the front and the back end section. Said metering device is however not supported or sustained or held in the area of the housing bottom side B, rather it is accessible for the user for example for applying pressure and/or for removing the metering device 100 out of the housing section 3.

The housing section 3 comprises an actuation device 7 by which the LED lamp 21 may be switched on/off or may be set in a predetermined light modus (intermittent, time-limited, only as long as pressure is applied on the actuation device 7 and so on).

The actuation device 7 is arranged on the housing rear R in the embodiments shown in the figures. It is further disposed—with respect to the longitudinal direction L of the metering apparatus—at the height or level of the front area of the metering device 100. Such arrangement advantageously enables the user to apply pressure on the reservoir 101 using thumb and middle finger in order to dispense light-curing material and subsequently or concurrently to operate the actuation device 7 using the index finger to cure the dispensed material. Thereby, the metering apparatus 1 may remain unchanged in the (same) hand both during dispensing and during curing. Reversing the metering apparatus 1, a change of grip etc. is omitted, making it easy and convenient to operate it.

It is well recognizable that the receiving device 5 and the LED lamp 21 are arranged such that a light cone 211 (or light circle) of the LED lamp 21 falls into an outlet area 103 of the metering device which is adjacent to an outlet opening for the light-curing material, e.g. adhesive material, hence lightening the exiting light-curing material.

The metering device 100 comprises a reservoir 101. Said reservoir 101 comprises light-curing material within its interior (not shown here). When pressure is being applied to the reservoir 101, for example by pressing with thumb and middle finger on the deformable outer surface of the reservoir 101 lying on opposite sides, the light curing material is thus conveyed into the metering channel 107 or is pressed out of it and conveyed into the outlet area 103. The outlet area 103 represents the connection of an interior of the metering device 100, in which the light-curing material is not exposed to ambient light, and an exterior of the metering device 100, in which the light-curing material is exposed to ambient light, or it represents a transition between the interior and the exterior.

The metering channel 107 may be purely exemplary inserted in a cover 105 of the metering device 100 until reaching a step. The metering channel 107 may be suitably fixed in the cover 105. The fixing may exemplarily be carried out by press fit, latching and/or gluing.

The metering channel 107 may be made of metal or alloy. It comprises for example the following dimensions: inner diameter 0.8 mm, outer diameter 1.2 mm, length e.g. about 12 mm.

The reservoir 101 of this embodiment is made of a first material, e.g. a soft polyethylene (e.g. LDPE—low density polyethylene) or comprises such material. The cover 105 is made of a third material—e.g. a harder polymer, in any case however a harder material compared to the first material—or comprises such material.

Both the first and the third material are selected (or processed, e.g. by a black or other type of coating or coloring) such that they are impervious to light—preferably, at least or in particular in a light wavelength range of 380 to 500 Nanometer (nm)—so that the light-curing material of the reservoir 1 and of the cover 105 are protected against undesired curing by light.

The connection between the reservoir 101 and the cover 105 is exemplarily executed through a threading, for example through a threading M10x1. Alternatively, the connection may be carried out by gluing, plugging etc., by way of example.

For further sealing, and also in order to prevent, when necessary, that the wall of the reservoir 101 which is stuck or plugged in the cover 105 does not get deformed, when applying pressure to the reservoir, due to the soft first material of the reservoir 101, a sealing ring, not shown here, (e.g. O-ring made of polymer) may be inserted in the area of a threading in the cover 105 to seal the reservoir 101. By screwing the metering device—in particular completely— onto the thread of the reservoir 101, the connection between these two components is thus sealed against an exterior by means of the sealing ring.

The housing section 3 comprises an LED lamp 21 as an example of a light-emitting device. The LED lamp, which can also be a flash-light device or another light source e.g. a laser or the like, is arranged in a protrusion 311 of the first end section. The LED lamp is optionally detachably (and thus replaceable) or undetachably connected to the housing section 3. The protrusion 311 has a smaller diameter, cross section area or a smaller cross section surface than the housing section 3, for example in the area of the first or the second holding section 51, 53. It is further recognizable in the figures that only the protrusion 311 with the LED lamp 21 and the metering channel 107 with the outlet opening are provided in the first end section 31. There can be a slot S of the housing section 3 between protrusion 311 and metering channel 107, as in the present example.

After applying the light-curing material it can be cured by light, in this exemplary embodiment by an LED light, preferably in the light wavelength between 390 and 405 nanometer (nm). This LED light is provided or exposed by the LED lamp 21 which is connected to the voltage source 23, arranged in the second end section 33, by means of an only indicated voltage line.

For further, optionally provided features of the metering device 100 reference is made to DE 10 2011 054 959 A1. Its relevant content is herewith made subject matter of the present disclosure by reference.

Figure 2:
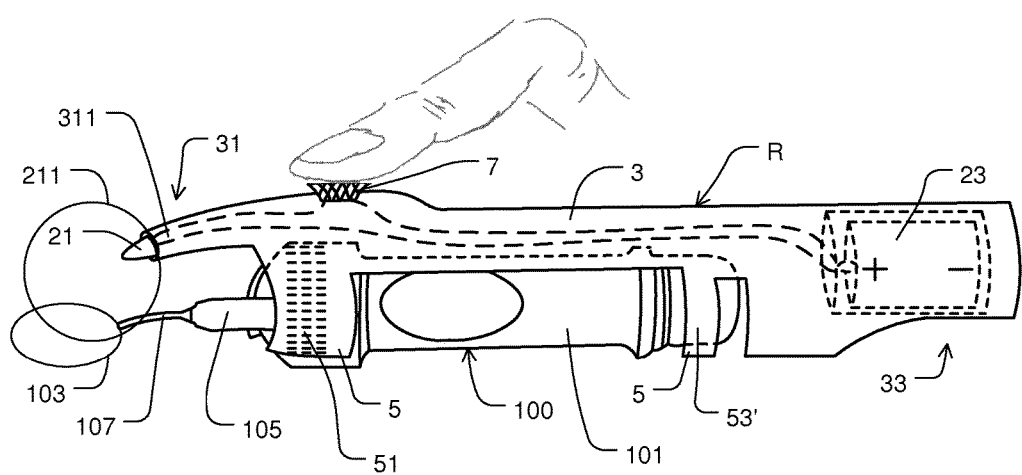
FIG. 2 shows a side view of a metering apparatus according to the present invention in a second embodiment.

FIG. 2 shows a metering apparatus 1 in a second embodiment according to the present invention. Said second embodiment differs from the first embodiment explained with regard to FIG. 1 solely in the design of its second holding section 53'.

The second holding section 53' does not comprise any spring element 29 being a metal spring. The holding effect of the holding section 53' is achieved in that it firmly clamps by means of a clamping device a rear section of the metering device 100 (which is arranged to the end of the metering device 100 which lies opposite to that end that carries the metering channel 105). The clamping device has two clamping jaws, by way of example. The clamping jaws may be pushed apart by means of the metering device 100 in order to insert the metering device 100 into the housing section 3 and bound or limit said metering device to the side, after its insertion, under pre-stressing, if necessary. The embodiment shown in FIG. 2 enables to dispense with a spring element. This facilitates and makes less costly the finishing of the housing section 3 or of the complete metering apparatus 1.

Figure 3:
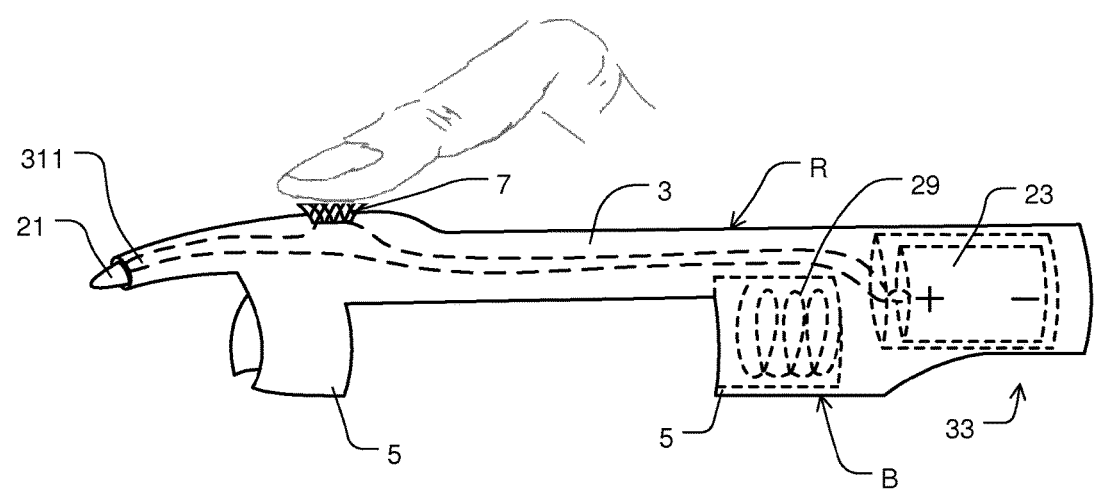
FIG. 3 shows a side view of the housing section of the metering apparatus of FIG. 1 without a metering device.

FIG. 3 shows a side view of the housing section 3 of the metering apparatus 1 of FIG. 1 without metering device, for clearer illustration of the housing section 3.

LIST OF REFERENCE NUMERALS

| Reference | Description |
|---|---|
| 100 | metering device |
| 101 | reservoir |
| 103 | outlet area |
| 105 | cover |
| 107 | metering channel |
| 1 | metering apparatus |
| 3 | housing section |
| 5 | receiving device |
| 51 | first holding section |

-continued

| Reference | Description |
|---|---|
| 53, 53' | second holding section |
| 7 | actuation device |
| 21 | LED lamp |
| 211 | light cone |
| 23 | voltage source |
| 29 | spring element |
| 31 | first end section |
| 311 | protrusion |
| 33 | second end section |
| L | longitudinal direction |
| R | housing rear |
| B | housing bottom side |
| S | slot |

The invention claimed is:

1. A metering apparatus, for metering, in a manually-controlled manner, a light-curing material, wherein the metering apparatus comprises
    a housing section which comprises at least a first end section and a second end section arranged opposite to the first end section;
    a receiving device for receiving, in a detachable manner, a metering device in which the light-curing material is contained and which comprises an outlet opening from which the light-curing material may exit; the receiving device being designed such that the outlet opening of the metering device faces the first end section of the housing section after being connected to the receiving device; and
    a light-emitting device for curing the light-curing material, arranged in or on the first end section of the housing section to be able, when actuated, to provide light towards or in a direction of the first end section of the housing section;
and wherein the receiving device is arranged such that a light-curing material exiting from the outlet opening of a metering device, received within the metering apparatus, enters into a light cone of the light-emitting device when being in use.

2. The metering apparatus of claim 1, wherein the receiving device comprises a holding section for receiving the metering device, the holding section being designed to tighten up or jam the metering device on the housing section or connect the metering device thereto by threading, latching or bayonet fixing or coupling.

3. The metering apparatus of claim 1, wherein the apparatus comprises a metering device received in the receiving device.

4. The metering apparatus of claim 3, wherein the metering device comprises a metering channel and an outlet opening of the metering channel as well as an outlet area through which light emitted by the light-emitting device enters or passes are provided in the first end section of the housing section itself.

5. The metering apparatus of claim 3, wherein the metering device comprises a metering channel, which metering channel is attached to the metering device by a Luer-lock system.

6. A metering apparatus, for metering, in a manually-controlled manner, a light-curing material, wherein the metering apparatus comprises
    a housing section which comprises at least a first end section and a second end section arranged opposite to the first end section;

a receiving device for receiving, in a detachable manner, a metering device in which the light-curing material is contained and which comprises an outlet opening from which the light-curing material may exit and further comprises a metering channel, which metering channel is attached to the metering device by a Luer-lock system; the receiving device being designed such that the outlet opening of the metering device faces the first end section of the housing section after being connected to the receiving device; and a light-emitting device for curing the light-curing material, arranged in or on the first end section of the housing section to be able, when actuated, to provide light towards or in a direction of the first end section of the housing section;

and wherein the housing section further comprises a housing rear and a housing bottom side and the receiving device is located in an area of the bottom side of the housing section.

7. The metering apparatus of claim 6, wherein the receiving device comprises a holding section for receiving the metering device, the holding section being designed to tighten up or jam the metering device on the housing section or connect the metering device thereto by threading, latching or bayonet fixing or coupling.

8. The metering apparatus of claim 6, wherein the receiving device comprises one or more holding sections, at least one of which has a ring-shaped or cylinder-shaped section for embracing or enfolding or encircling the metering device along a part of a circumference thereof, which ring-shaped or cylinder-shaped section comprises a gap or split or slot along which it does not completely embrace the circumference of the metering device.

9. The metering apparatus of claim 6, wherein the receiving device comprises a first holding section and a second holding section for receiving, in a detachable manner, the metering device, the first holding section being arranged closer to the first end section than the second holding section, and at least one of the first and second holding sections comprising an adaption section which is movable in a longitudinal direction of the housing section.

10. The metering apparatus of claim 6, wherein the receiving device comprises a first holding section and a second holding section for receiving, in a detachable manner, the metering device, the first and second holding sections being arranged such that they embrace or enfold a front and a back end section of the metering device but not a middle section thereof that is disposed between the front and back end section.

11. The metering apparatus of claim 6, wherein an actuation device for switching the light-emitting device on or off is a part of the rear of the housing, corresponds thereto or is attached thereto.

12. A metering apparatus, for metering, in a manually-controlled manner, a light-curing material, wherein the metering apparatus comprises a housing section which comprises at least a first end section and a second end section arranged opposite to the first end section;

a receiving device for receiving, in a detachable manner, a metering device in which the light-curing material is contained and which comprises an outlet opening from which the light-curing material may exit and further comprises a metering channel, which metering channel is attached to the metering device by a Luer-lock system; the receiving device being designed such that the outlet opening of the metering device faces the first end section of the housing section after being connected to the receiving device; and a light-emitting device for curing the light-curing material, arranged in or on the first end section of the housing section to be able, when actuated, to provide light towards or in a direction of the first end section of the housing section;

and wherein the receiving device comprises one or more holding sections for receiving, in a detachable manner, the metering device, at least one of the one or more holding sections having a ring-shaped or cylinder-shaped section for embracing or enfolding or encircling the metering device along a part of a circumference thereof, which ring-shaped or cylinder-shaped section comprises a gap or split or slot along which it does not completely embrace the circumference of the metering device.

13. The metering apparatus of claim 12, wherein the one or more holding sections of the receiving device comprise a first holding section and a second holding section, the first holding section being arranged closer to the first end section than the second holding section, and at least one of the first and second holding sections comprising an adaption section which is movable in a longitudinal direction of the housing section.

14. The metering apparatus of claim 12, wherein the one or more holding sections of the receiving device comprise a first holding section and a second holding section, the first and second holding sections being arranged such that they embrace or enfold a front and a back end section of the metering device but not a middle section thereof that is disposed between the front and back end sections.

* * * * *